United States Patent
Kong et al.

(10) Patent No.: US 9,669,005 B2
(45) Date of Patent: Jun. 6, 2017

(54) USE OF NARINGENIN IN PREPARING DRUGS FOR PREVENTING AND/OR TREATMENT ABDOMINAL AORTIC ANEURYSM

(71) Applicant: Peking University, Beijing (CN)

(72) Inventors: Wei Kong, Beijing (CN); Qinghua Cui, Beijing (CN); Jingang Zheng, Beijing (CN); Ziyi Liu, Beijing (CN); Fang Yu, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 0 days.

(21) Appl. No.: 14/901,692

(22) PCT Filed: Jan. 24, 2014

(86) PCT No.: PCT/CN2014/000093
§ 371 (c)(1),
(2) Date: Dec. 28, 2015

(87) PCT Pub. No.: WO2014/206056
PCT Pub. Date: Dec. 31, 2014

(65) Prior Publication Data
US 2016/0367523 A1     Dec. 22, 2016

(30) Foreign Application Priority Data
Jun. 27, 2013  (CN) .......................... 2013 1 0264289

(51) Int. Cl.
*A61K 31/353* (2006.01)
(52) U.S. Cl.
CPC .................................. *A61K 31/353* (2013.01)
(58) Field of Classification Search
None
See application file for complete search history.

(56) References Cited

FOREIGN PATENT DOCUMENTS

| CN | 102302483 A | 1/2012 |
| CN | 103340849 A | 10/2013 |

OTHER PUBLICATIONS

Chen, S. et al., Food and Chemical Technology 2012 vol. 50 pp. 3025-3031.*
Miyake, Gene Therapy 2006 vol. 13, pp. 695-670.*
Chen et al., "Naringenin Inhibits TNF-α Induced VSMC Proliferation and Migration via Induction of HO-1," Food and Chemical Toxicology., 50 (2012): 3025-3031, Jun. 16, 2012.
Miyake et al., "Prevention of Abdominal Aortic Aneurysms by Simultaneous Inhibition of NFkB and ets Using Chimerio Decoy Oligonucleotides in a Rabbit Model," Gene Theraphy, Nature Publishing Group, 2006, pp. 695-704.
Tieu et al., "An Adventitial IL-6/MCP1 Amplification Loop Accelerates Macrophage-mediated Vascular Inflammation Leading to Aortic Dissection in Mice," The Journal of Clinical Investigation, Dec. 2009, pp. 3637-3651, vol. 119, No. 12.
Ishibashi et al., "Bone Marrow-Derived Monocyte Chemoattractant Protein-1 Receptor CCR2 Is Critical in Angiotensin Il-Induced Acceleration of Atherosclerosis and Aneurysm Formation in Hypercholesterolemic Mice," Arteriosclerosis Thrombosis Vascular Biology, Nov. 2004, pp. e174-e.178, American Heart Association, Inc.
MacTaggart et al., "Deletion of CCR2 But Not CCR5 or CXCR3 Inhibits Aortic Aneurysm Formation," Surgery Research, University of Nebraska Medical Center, Apr. 27, 2007, pp. 284-288, Mosby, Inc., Omaha, Nebraska.
Morcos, et al., "A Grapefruit a Day for Patients Infected with Hepatitis C?" Heptology, Jun. 2008, pp. 2141-2142, vol. 47, No. 6, American Association for the Study of Liver Diseases.
Mulvihill, et al., "Naringenin Prevents Dyslipidemia, Apolipoprotein B Overproduction, and Hyperinsulinemia in LDL Receptor—Null Mice with Diet-Induced Insulin Resistance," Diabetes, Oct. 2009, pp. 2198-2210, vol. 58, American Diabetes Association.
Baxter et al., "Prolonged Administration of Doxycycline in Patients with Small Asymptomatic Abdominal Aortic Aneurysms: Report of a Prospective (Phase II) Multicenter Study," Journal of Vascular Surgery, Jul. 2002, pp. 1-12, The Society for Vascular Surgery and the American Association for Vascular Surgery.
Holmes et al., "Indomethacin Prevents Elastase-Induced Abdominal Aortic Aneurysms in the Rat," Journal of Surgical Research, 1996, pp. 305-308, Article No. 0265, Academic Press, Inc.
Walton et al., "Inhibition of Prostaglandin E2 Synthesis in Abdominal Aortic Aneurysms: Implications for Smooth Muscle Cell Viability, Inflammatory Processes, and the Expansion of Abdominal Aortic Aneurysms," Circulation, Jul. 6, 1999, pp. 48-54, American Heart Association, Inc.
Mosorin et al., "Use of Doxycycline to Decrease the Growth Rate of Abdominal Aortic Aneurysms: A Randomized, Double-Blind, Placebo-controlled Pilot Study," Journal of Vascular Surgery, 2001, pp. 606-610, vol. 34, No. 4, The Society for Vascular Surgery and the American Association for Vascular Surgery.

(Continued)

*Primary Examiner* — Heidi Reese
(74) *Attorney, Agent, or Firm* — Knobbe Martens Olson & Bear, LLP (57) ABSTRACT

Naringenin is used for preparing products for preventing and/or treating abdominal aortic aneurysms. The products include drugs and/or health care products. The products were tested in two clinically associated abdominal aortic aneurysm disease models: using angiotensin II (1000 ng/kg/min) through subcutaneous submerging pump to induce ApoE knockout mice; and using calcium phosphate (0.5 M) to daub the abdominal aortas of locally induced C57 mice with abdominal aortic aneurysms. Experiments demonstrate that orally administered naringenin can significantly inhibit the onset and development of an abdominal aortic aneurysm in the $CaPO_4$ daubed and AngII submerging pump induced mice. Thus, naringenin can be used in the treatment of patients with abdominal aortic aneurysms.

6 Claims, 9 Drawing Sheets

(56) References Cited

OTHER PUBLICATIONS

Gadowski et al., "Abdominal Aortic Aneurysm Expansion Rate: Effect of Size and Beta-Adrenergic Blockade," Journal of Vascular Surgery, Apr. 1994, pp. 727-731, vol. 19, No. 4, The Society for Vascular Surgery and International Society for Cardiovascular Surgery, North American Chapter.

Vammen et al., "Randomized Double-Blind Controlled Trial of Roxithromycin for Prevention of Abdominal Aortic Aneurysm Expansion," British Journal of Surgery, 2001, pp. 1066-1072, Blackwell Science Ltd.

Schouten et al., "Statins are Associated with a Reduced Infrarenal Abdominal Aortic Aneurysm Growth," Eur J. Vasc. Endovasc. Surgery, 2006, pp. 21-26, vol. 32, Elsevier Ltd.

Daugherty et al., "Mouse Models of Abdominal Aortic Aneurysms," Arteriosclerosis, Thrombosis, and Vascular Biology, Mar. 2004, pp. 429-434, American Heart Association, Inc., Greenville Avenue, Dallas, TX.

Dubost et al., "Resection of an Aneurysm of the Abdominal Aorta: Reestablishment of the Continuity by a Preserved Human Arterial Graft, with Result After Five Months," A.M.A Archives of Surgery, downloaded Feb. 25, 2016, Paris, France.

Johnston et al., "Suggested Standards for Reporting on Arterial Aneurysms," Journal of Vascular Surgery, Mar. 1991, pp. 452-458, vol. 13, No. 3.

International Search Report dated May 8, 2014 for PCT/CN2014/000093.

Mulvihill, et al., "Naringenin Decreases Progression of Atherosclerosis by Improving Dyslipidemia in High-Fat-Fed Low-Density lipoprotein Receptor-Null Mice," Arterioscler Thromb Vasc Biol, Apr. 2010.

Lou et al., "Naringenin Decreases Invasiveness and Metastasis by Inhibiting TGF-β-Induced Epithelial to Mesenchymal Transition in Pancreatic Cancer Cells," PLOS ONE, Dec. 26, 2012, pp. 1-9, Lou et al, vol. 7, Issue 12.

* cited by examiner

A in situ zymography

USE OF NARINGENIN IN PREPARING DRUGS FOR PREVENTING AND/OR TREATMENT ABDOMINAL AORTIC ANEURYSM

CROSS REFERENCE TO RELATED APPLICATIONS

This application is the U.S. National Phase of International Application No. PCT/CN2014/000093, filed Jan. 24, 2014, designating the U.S. and published in Chinese as WO 2014/206056 on Dec. 31, 2014 which claims the benefit of Chinese Patent Application No. 201310264289.3, filed Jun. 27, 2013. Any and all applications for which a foreign or domestic priority claim is identified here or in the Application Data Sheet as filed with the present application are hereby incorporated by reference under 37 CFR 1.57.

TECHNICAL FIELD

The present application relates to use of naringenin in pharmaceutical field.

BACKGROUND

An abdominal aortic aneurysm (AAA) is a cardiovascular disease with high lethality. It refers to a permanent expansion of an abdominal aortic wall, and if the expansion of the wall is greater than 50% of diameter of adjacent site, or diameter thereof exceeds 3 cm, it can be considered to suffer from an abdominal aortic aneurysm (Johnston K W, Rutherford R B, Tilson M D, Shah D M, Hollier L, Stanley J C. Suggested standards for reporting on Subcommittee on Reporting Standards for Arterial Aneurysms, Ad Hoc Committee on Reporting Standards, Society for Vascular Surgery and North American Chapter, International Society for Cardiovascular Surgery. J Vasc Surg. 1991; 13(3):452-458). Once the aneurysmal aorta ruptures, the patient will die from massive blood loss, therefore, an abdominal aortic aneurysm is also called as "the time bomb in the human body". This disease usually happens in older people, especially in male. The incidence gradually rises with age, and can be up to 8-10%, and the fatality rate reaches to 50%-80%. In USA, the death caused by rapture of an abdominal aortic aneurysm ranks fifteenth in all causes of death and tenth in causes of death of adult male diseases. While in PRC, in the recent 30 years, the incidence thereof rapidly rises by 3 times. However, the pathogenesis and risk factors about this disease are not very clear up to now, therefore, there is no effective method for early prevention, early warning, and drug prevention and treatment. Since DuBost firstly successfully implemented abdominal aortic aneurysm resection and artificial vascular graft at 1951 (DuBost C, Allary M, Oeconomos N. Resection of an aneurysm of the abdominal aorta: reestablishment of the continuity by a preserved human arterial graft, with result after five months. AMA Arch Surg. 1952 March; 64(3):405-8), with the continuous development and improvement of technologies, an endovascular repair has been widely accepted and used worldwidely, and becomes a most commonly used method for treating an abdominal aortic aneurysm at present. However, there are many disadvantages in the surgery, such as high-risk, expensive, not a permanent cure, and difficult to popularize. And as for the patient having a small abdominal aortic aneurysm, that is, when the aneurysmal aorta diameter is less than 5.5 cm, the risk of rupture may be less than the risk of surgery. However, there is no effective drug which can prevent and treat an abdominal aortic aneurysm at present, therefore, exploring a prevention and treatment method for the treatment of abdominal aortic aneurysms now has become a focus and hotspot for cardiovascular research.

A research shows that the pathogenesis of an abdominal aortic aneurysm is mainly due to rise in reactive oxygen species (ROS) of vascular walls, increase in infiltration of inflammatory cells and release of inflammatory cytokines, rise in activities of matrix metalloproteinases (NMP), causing inflammatory response of vascular walls and significant increase of matrix degradation, thereby to result in the onset of abdominal aortic aneurysms (Daugherty A, Cassis L A. Mouse models of abdominal aortic aneurysms. Arterioscler Thromb Vasc Biol. 2004 March; 24(3):429-34). This suggests if drugs for inhibiting vascular inflammatory response or reducing matrix degradation are used, onset and development of abdominal aortic aneurysms may be alleviated or treated. At present, there lacks specific drug treatment schemes supported by large-scale clinical randomized control studies. However, there once are small-scale clinical trials for some drugs for treating abdominal aortic aneurysms, such as statins (Schouten D et al. Statins are Associated with a Reduced Infrarenal Abdominal Aortic Aneurysm Growth. Eur J Vasc Endovasc Surg. 2006 32, 21-26.), macrolide antibiotics (Vammen S et al. Randomized double-blind controlled trial of roxithromycin for prevention of abdominal aortic aneurysm expansion. Br J Surg 2001 88(8):1066-1072), adrenergic receptor blockers (Gregory R et al. Abdominal aortic aneurysm expansion rate: Effect of size and beta-adrenergic blockade. J Vasc Surg.1994 April; 19(4):727-31), and doxycycline (Mosorin M et al. Use of doxycycline to decrease the growth rate of abdominal aortic aneurysms: a randomized, double-blind, placebo-controlled pilot study. J Vasc Surg 2001 34(4):606-610), etc., and they all have a certain therapeutic effect on the patients having abdominal aortic aneurysms. In addition, an inhibitor of prostaglandin synthetase (Walton L J et al. Inhibition of prostaglandin E2 synthesis in abdominal aortic aneurysms: implications for smooth muscle cell viability, inflammatory processes, and the expansion of abdominal aortic aneurysms. Circulation.1999 100(1):48-54) and an anti-inflammatory drug, indomethacin, (Holmes D R et al. Indomethacin prevents elastase-induced abdominal aortic aneurysms in the rat. J Surg Res. 1996 June; 63(1):305-9.) also have a certain effect in animal models in which abdominal aortic aneurysms are induced. Most of these drugs are indicated to reduce the inflammatory response of blood vessels, or inhibit the activities of metalloproteinases, thereby to function. However, the above drugs all lack evidences of large-scale randomized control clinical study supporting effectiveness thereof. When applied to clinical trials, some drugs, such as doxycycline, also produce frequent side effects (Baxter B T et al. Prolonged administration of doxycycline in patients with small asymptomatic abdominal aortic aneurysms: report of a prospective (Phase II) multicenter study. J Vasc Surg. 2002 July; 36(1):1-12). Therefore, it will have enormous clinical application value to develop a new drug possessing good prevention and treatment effects and a few side effects for treating abdominal aortic aneurysms.

Naringenin is a natural flavonoids compound, which are highly expressed flavonoids in citrus plants such as grapefruit, shaddock peel, orange peel, and potato peel, and in traditional Chinese medicine, such as Huyou peel, phellinus igniarius, and Ilex centrochinensis. In animal experiments, it has been reported that naringenin can reduce blood fat, and reduce the levels of cholesterol, triglycerides, and low density lipoprotein (LDL-C) in serum, thereby to reduce onset and development of atherosclerosis (Mulvihill E, Assini J, Sutherland B, DiMattia A, Khami M, Koppes J, Sawyez C, Whitman S, Huff M. in High-Fat-Fed Low-Density Lipoprotein Receptor-Null Mice Naringenin Decreases Progression of Atherosclerosis by Improving Dyslipidemia. Arterioscler Thromb Vasc Biol 2010, 30:742-748). It also can regulate immune function and inhibit tumor growth (Lou C, Zhang F, Yang M, Zhao J, Zeng W, Fang X, Zhang Y, Zhang C, Liang W. Naringenin Decreases Invasiveness and Metastasis by Inhibiting TGF-β-Induced Epithelial to Mesenchymal Transition in Pancreatic Cancer Cells. PLoS ONE 2012; 7(12).). In addition, naringenin also can treat insulin resistance and Type II diabetes (Mulvihill E E, Allister E M, Sutherland B G, Telford D E, Sawyez C G, Edwards J Y, Markle J M, Hegele R A, Huff M W. Naringenin prevents dyslipidemia, apolipoprotein B overproduction, and hyperinsulinemia in LDL receptor-null mice with diet-induced insulin resistance. Diabetes. 2009; 58(10): 2198-210), as well as hepatopathy (Morcos P N, Brennan B, Smith P F. A grapefruit a day for patients infected with hepatitis C Hepatology. 2008 June; 47(6):2141-2) in animal models. However, there are no relevant reports about use of naringenin for prevention and treatment of the onset of abdominal aortic aneurysms.

SUMMARY

The purpose of the present invention is to provide a new use of naringenin as a drug.

The use of naringenin provided in the present invention is the use of them for preparing products for preventing and/or treating abdominal aortic aneurysms. The products comprise drugs and/or health care products.

Further use of said naringenin also can comprise at least one of the following:

1) use for preparing drugs for inhibiting fracture of abdominal aorta elastic lamina;
2) use for preparing drugs for inhibiting infiltration of inflammatory cells of abdominal aorta vascular walls; the inflammatory cell can be macrophage and/or leukocyte;
3) use for preparing drugs for inhibiting the levels of IL-6 and MCP-1 in plasma;
4) use for preparing drugs for inhibiting the expressions of inflammatory factors in abdominal aorta vascular walls; the inflammatory factors can be interleukin IL-6 and/or monocyte chemotactic factor MCP-1;
5) use for preparing drugs for inhibiting the activity and expression of matrix metalloproteinase of abdominal aorta vascular walls; the matrix metalloproteinase specifically can be MMP-9.

The drugs prepared by employing naringenin as an active ingredient for preventing and/or treating abdominal aortic aneurysms also fall into the protection scope of the present invention.

The drugs can be introduced into the body such as muscle, intracutaneous, subcutaneous, vein, and mucosal tissues via the methods of injection, spraying, nasal drip, eye drip, permeation, absorption, or physical or chemical intervention; or can be introduced into the body after mixed with other substances or encapsulated by other substances.

When needed, one or more pharmaceutically acceptable carriers can be added to the above drugs. The carriers comprise conventional diluents, excipients, fillers, binders, humectants, disintegrating agents, absorption enhancers, surfactants, adsorption carriers, lubricants, etc.

The drugs can be prepared into various forms such as injections, suspending agents, powders, tablets, granules, and the like. The above various dosage forms of drugs can be prepared according to conventional methods of the pharmaceutical field.

The present invention uses two clinically associated abdominal aortic aneurysm disease models: using angiotensin II (1000 ng/kg/min) through subcutaneous submerging pump to induce ApoE knockout mice; and using calcium phosphate (0.5 M) to daub the abdominal aortas of locally induced C57 mice with abdominal aortic aneurysms. Experiments demonstrate that naringenin via oral gavage can significantly inhibit the onset and development of an abdominal aortic aneurysm in the $CaPO_4$ daubed and AngII submerging pump induced mice, and thereby naringenin can be used in the treatment of patients with abdominal aortic aneurysms.

The drugs for preventing and/or treating abdominal aortic aneurysms provided by the present invention are safe and low toxic, and the pharmacologic effects thereof are stronger; sources of raw materials thereof are rich, wide, inexpensive, and can be obtained from crude product or monomer of Naringin by a hydrolysis method, or obtained by extracting from various crude medicines containing naringenin, or obtained by using other chemical synthesis methods; the cost is low, the process is simple, and the yield is high; and the curative effect is definite, and the effective dose is low. The present invention provides a new drug source for preventing, diagnosing, detecting, protecting, treating, and studying abdominal aortic aneurysm diseases, it is easy to popularize and apply, and it can produce huge social and economic benefits within a short period of time.

BRIEF DESCRIPTION

A shows the diameters of infrarenal arteries of C57BL/6J mice with NaCl daubing and feeding water, $CaPO_4$ daubing and feeding water, naringenin or doxycycline, identified by histological staining, and the statistical situation thereof; and B shows the fracture degree of infrarenal arterial elastic lamina of C57BL/6J mice with NaCl daubing and feeding water, $CaPO_4$ daubing and feeding water, naringenin or doxycycline identified by histological staining, and the statistical situation thereof.

A shows the reduction of the inflammatory cell (macrophage and leukocyte) infiltration in vascular walls of infrarenal arteries of C57BL/6J mice via naringenin or doxycycline gavage identified by immunohistochemistry; and B shows the reduction of the inflammatory factor (interleukin IL-6/monocyte chemotactic factor MCP-1) expression in vascular walls of infrarenal arteries of C57BL/6J mice via naringenin or doxycycline gavage identified by immunohistochemistry.

A shows the inhibition of the activity of $CaPO_4$ induced matrix metalloproteinase NMP with naringenin or doxycycline validated by in situ zymography; and B shows the inhibition of the activities of $CaPO_4$ induced NMP 2 and NMP-9 with naringenin or doxycycline validated by gelatin zymography.

A is a series of vascular photos showing the onset situation of abdominal aortic aneurysms in $ApoE^{-/-}$ mice which are gavaged with naringenin; and B is a statistical graph showing the morbidity of abdominal aortic aneurysms in $ApoE^{-/-}$ mice which are gavaged with naringenin.

A shows the maximum diameter of suprarenal aortas of mice which are gavaged with naringenin or water, identified by histological staining, the statistical situation thereof; and B shows the fracture degree of elastic lamina of suprarenal aortas of mice which are feed on naringenin or water identified by histological staining, and the statistical situation thereof.

A shows the reduction of inflammatory cell infiltration in vascular walls of angiotensin II induced $ApoE^{-/-}$ mice via naringenin gavage identified by immunohistochemistry.

B shows the reduction of the expressions of inflammatory factors in the plasma of angiotensin II induced $ApoE^{-/-}$ mice by naringenin gavage; and C shows the reduction of the release of inflammatory factors in vascular walls of mice by naringenin gavage.

A shows the inhibition of the activities of angiotensin II induced matrix metalloproteinases via naringenin validated by in situ zymography.

B shows the inhibition of the activity of angiotensin II induced NMP-2 and NMP-9 via naringenin validated by gelatin zymography.

A is series of vascular photos showing the onset of aneurysms in mice after the second round of angiotensin II treatment.

B shows incidence rate % of ApoE knockout mice in which aneurysms previously have formed after the second round of angiotensin II submerging pump treatment, relative to the number of mice in which aneurysm previously had formed.

C is a quantification figure of the maximum diameter of abdominal aortas of mice via ultrasonic testing; and D shows the effect of naringenin on the activities of metalloproteinases NMP-9 and NMP-2 of suprarenal abdominal aortas of ApoE knockout mice, detected by gelatin zymography; each group of 3 mice.

DETAILED DESCRIPTION

The present invention will be described through the following specific Examples, but the present invention is not limited to these.

Unless expressly indicated otherwise, the experimental methods described in the following Examples are all conventional methods; and unless expressly indicated otherwise, all the reagents and biological materials can be commercially available.

EXAMPLE 1

The Reduction of the Onset of Abdominal Aortic Aneurysms in C57BL/6J Mice with $CaPO_4$ Daubed Infrarenal Arteries by Naringenin Gavage 1. Models of Abdominal AAortic neurysms Induced by $CaPO_4$ Daubed Infrarenal Aortas of Mice 12-week old of male C57BL/6 mice were anesthetized via intraperitoneal injection of 0.1% pentobarbital sodium (injection according to body weight, 6-7 l/g). Infrarenal abdominal aortas were separated, and the separated infrarenal abdominal aortas were packaged by gauze (1 cm in width×3 cm in length) soaked in 0.5 M $CaCl_2$ solution. After 10 minutes, the gauze was removed, gauze soaked in PBS was instead used to package the blood vessel for 5 min. $CaCl_2$+and $PO_4^{-3}$ in PBS can form $CaPO_4$ crystal, that is, corresponding to daubing $CaPO_4$ to the blood vessel. After packaging the blood vessel with gauze soaked in NaCl for 10 minutes, gauze soaked in PBS is instead used for 5 min, serving as NaCl daubed control group.

2. Models of Naringenin (NGN) or Doxycycline (Dox) Gavage Doxycycline was used as a Positive Control Drug.

Figure 1:
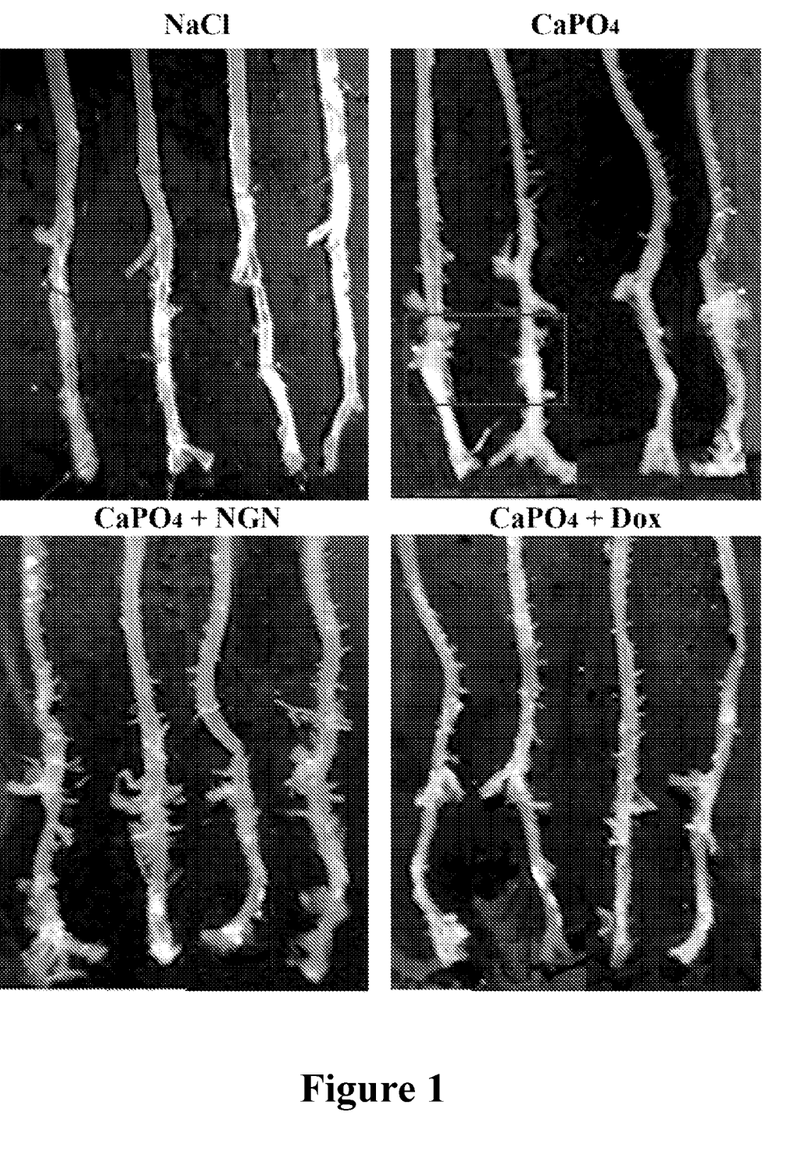
FIG. 1 is a series of vascular photos showing the reduction of the onset of abdominal aortic aneurysms in C57BL/6J mice with $CaPO_4$ daubed infrarenal arteries by naringenin (NGN) gavage, wherein doxycycline (Dox) is used as a positive control of animal experiments.

Gavage was started at the first day after surgery, and water, naringenin (50 mg/kg) (Sigma-Aldrich, St. Louis, Mo.) or doxycycline (100 mg/kg) (Sigma-Aldrich, St. Louis, Mo.) gavage were given on mice daily. Materials were removed from the mice 7 days after gavage. Mice were weighed, and blood was drawn from inner canthus by capillary, after centrifuged for 10 minutes at 6000 rotations, the supernatant was removed and blood fat was measured (kit is purchased from BIOSINO company). Then perfusion and washing were performed on mice using PBS. Blood vessels were separated, and four blood vessels were randomly chosen for each group for photographing. The results were shown in FIG. 1, wherein, NaCl was the group of daubing NaCl (n=11), $CaPO_4$ was the group of daubing $CaPO_4$ plus water feed (n=12), $CaPO_4$+NGN was the group of daubing $CaPO_4$ μlus naringenin gavage (n=11), and $CaPO_4$+Dox was the group of daubing $CaPO_4$ μlus doxycycline gavage (n=11). The results demonstrate that, compared with mice in the group of daubing NaCl, the blood vessels at infrarenal site in $CaPO_4$ daubed mice exhibit significant bulge, while naringenin or doxycycline gavage can reduce the incidence rate and degree of bulge.

The blood vessels were sliced, and the change of the diameters in infrarenal abdominal aortas of mice were identified by H.E. staining. The results were shown in FIG. 2A, and $CaPO_4$ daubing can significantly increase the diameters of infrarenal blood vessels of mice, compared with the group of daubing NaCl (NaCl vs. $CaPO_4$, 0.77±0.06 vs. 1.40±0.19 mm, P<0.05). However, naringenin or doxycycline gavage daily can significantly reduce the hemangiectasis caused by $CaPO_4$ daubing, and the effects of naringenin and doxycycline are similar ($CaPO_4$+NGN vs. $CaPO_4$+Dox, 1.03±0.18 vs. 0.99±0.18 mm). The data in FIG. 2A were an average value±standard deviation.

Figure 2:
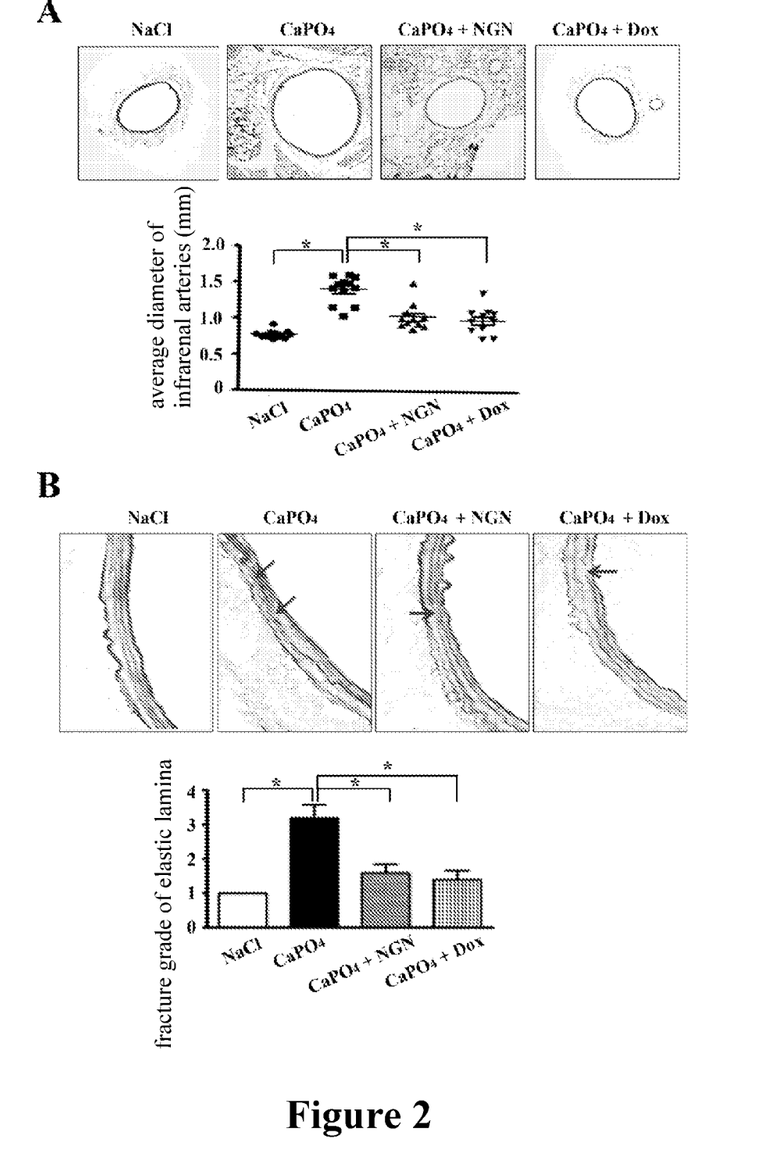
FIG. 2 shows the reduction of the severity of abdominal aortic aneurysms in C57BL/6J mice with $CaPO_4$ daubed infrarenal arteries by naringenin (NGN) gavage, wherein doxycycline is used as a positive control of animal experiments.

The fracture degree of elastic lamina is also an index showing the severity of abdominal aortic aneurysms. The degradation of elastic lamina is divided into four grades. The first grade means that the degradation of elastic lamina is less than 25%, with the second grade of 25%-50%, the third grade of 50%-75%, and the fourth grade means the fracture is more than 75%. We used Gomori staining to identify the fracture situation of elastic lamina of infrarenal abdominal aortas of mice. The results were shown in FIG. 2B, compared with NaCl daubing, $CaPO_4$ daubing significantly increase the fracture situation of elastic lamina of infrarenal abdominal aortas of mice, while naringenin or doxycycline gavage can reverse the effect of $CaPO_4$. The data in FIG. 2B were an average value±standard deviation.

In addition, naringenin gavage does not affect the body weights and blood fat levels of C57BL/6J mice, see Table 1.

TABLE 1 the biochemical indexes of $CaPO_4$ treated C57BL/6J mice

| Group | Number | Body weight (g) | Cholesterol (mmol) | Triglyceride (mmol) |
|---|---|---|---|---|
| NaCl | 11 | 21.1 ± 1.92 | 3.09 ± 0.37 | 1.22 ± 0.32 |
| $CaPO_4$ | 12 | 20.3 ± 1.98 | 3.73 ± 0.93 | 1.22 ± 0.39 |
| $CaPO_4$ + NGN | 11 | 20.1 ± 1.41 | 3.53 ± 0.45 | 0.97 ± 0.22 |
| $CaPO_4$ + Dox | 11 | 21.0 ± 1.89 | 3.49 ± 0.64 | 1.07 ± 0.32 |

Figure 3:
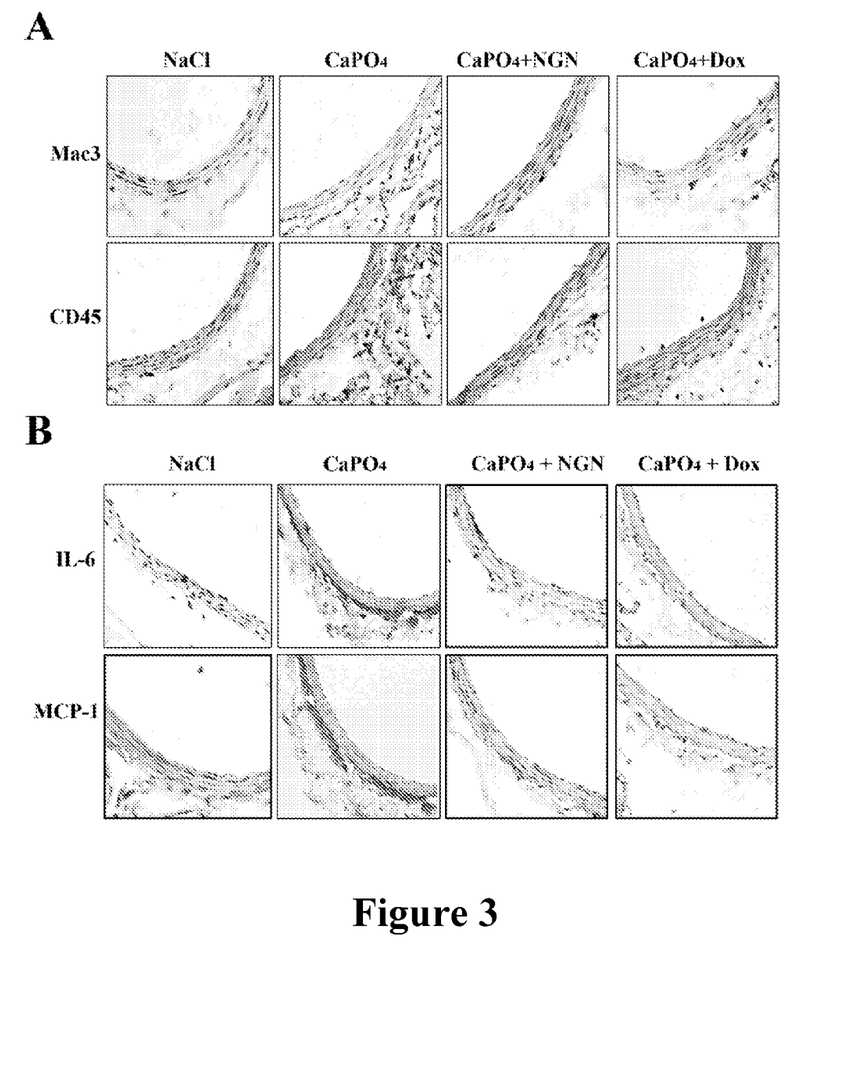
FIG. 3 shows the reduction of the inflammatory response of infrarenal arterial vessel in $CaPO_4$ daubed C57BL/6J mice by naringenin or doxycycline.

In the onset of abdominal aortic aneurysm, inflammatory cell infiltration of vascular walls is a common feature. We used histochemical staining to identify inflammatory cells infiltrated in vascular walls. Mac3 is the result of immumohistochemical staining on anti-Mac3 specific antibody, representative of macrophage, and CD45 is the result of immumohistochemical staining on anti-CD45 specific antibody, representative of leukocyte. The results were shown in FIG. 3A. $CaPO_4$ daubing can significantly increase the infiltration of macrophages and leukocytes in adventitia in vascular walls, while naringenin or doxycycline gavage can reduce such effect.

IL-6 and MCP-1 are proinflammatory chemotactic factors and cytokines, and they are mainly from vascular walls. MCP-1 can release more matrix metalloproteinase to degrade matrix by recruiting leukocytes, which mediats vascular remodeling and expanding (MacTaggart J N et al. Deletion of ccr2 but not ccr5 or cxcr3 inhibits aortic aneurysm formation Surgery. 2007; 142:284-288; Ishibashi M et al. Bone marrow-derived monocyte chemoattractant protein-1 receptor ccr2 is critical in angiotensin ii-induced acceleration of atherosclerosis and aneurysm formation in hypercholesterolemic mice. Arterioscl throm vasc biol. 2004; 24: e174-178), while IL-6 can enlarge effect of MCP-1 to aggravate the onset of abdominal aortic aneurysms (Tieu B C et al. An adventitial il-6/mcp1 amplification loop accelerates macrophage-mediated vascular inflammation leading to aortic dissection in mice. J Clin Invest. 2009; 119:3637-3651). We used histochemical staining to identify the expressions of IL-6 and MCP-1 on vascular walls. IL-6 and MCP-1 were immunohistochemical results of anti-IL-6 and anti-MCP-1 specific antibodies (purchased from Abcam, Cambridge Company, UK), respectively. The results were shown in FIG. 3B. $CaPO_4$ daubing can significantly increase the expression of IL-6 and MCP-1 in adventitia in vascular walls, while naringenin or doxycycline gavage can reduce their expressions.

Figure 4:
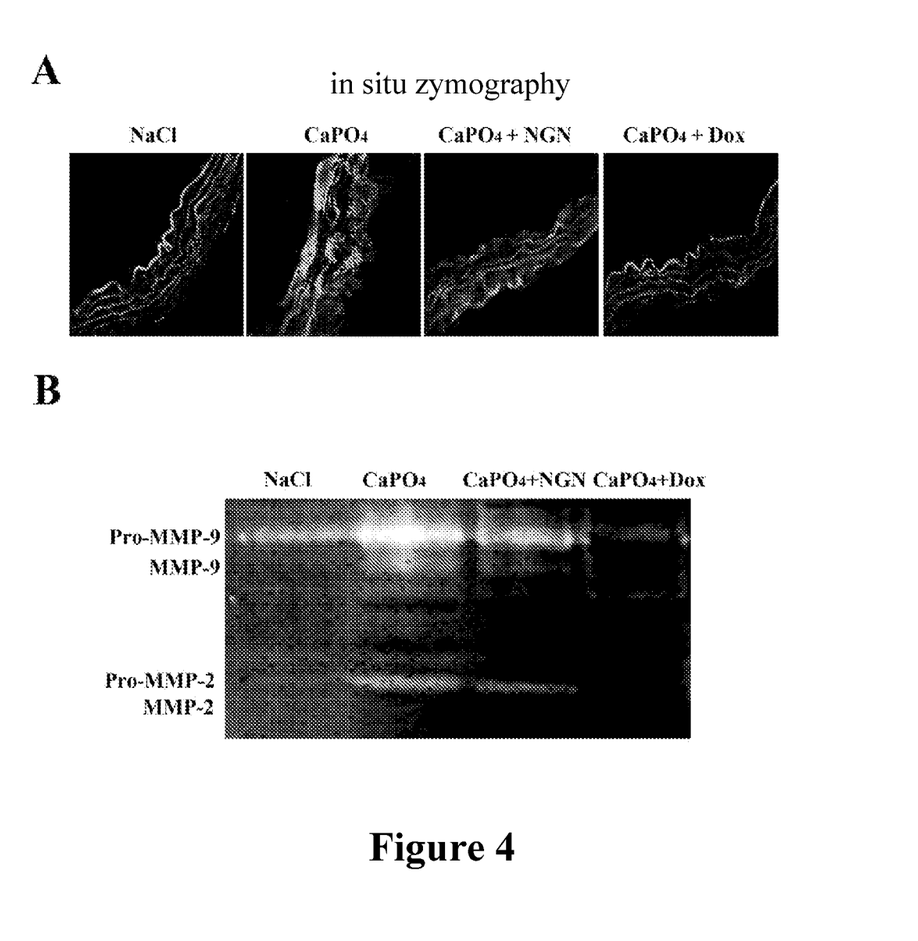
FIG. 4 shows the inhibition of the activities and expressions of matrix metalloproteinases in vascular walls of infrarenal arteries of $CaPO_4$ daubed C57BL/6J mice by naringenin or doxycycline.

One of pathogenesis of an abdominal aortic aneurysm is activation of matrix metalloproteinase, activity of which increases, which can significantly increase the degradation of matrix, thereby to cause the onset of an abdominal aortic aneurysm. After the aortas of mice were perfused with PBS, fresh tissue was directly embedded with OCT, put in liquid nitrogen for freezing, and then continuously sliced. Firstly, washing was performed with PBS for 3 min, thrice. A fluorescently labeled DQ-gelation-FITC substrate (Sigma-Aldrich, St. Louis, Mo.) was incubated 1 hour at 37° C. Under normal circumstances, fluorescent label for the substrate was packaged, so there is no fluorescence; after activated gelatinase degraded gelatin, green fluorescent label would be exposed. After the section was incubated, washing was performed with PBS for 3 min, thrice, and then the section was sealed. Immunofluorescence confocal microscopy was used to irradiate. The stronger fluorescence was, which means, the stronger activity of matrix metalloproteinase was. The results of in situ zymography were shown in FIG. 4A, $CaPO_4$ daubing significantly increases the activity of matrix metalloproteinase, while naringenin or doxycycline gavage can reduce the activity of matrix metalloproteinase induced by $CaPO_4$ daubing.

3. Gelatin Zymography

After extravasated blood in fresh removed blood vessels of infrarenal site in abdominal aortas of mice were cleared, and fat and connective tissues were removed, and blood vessels were cut into 1 cm ring, and put into 24-well plate. Blood vessels were cultured for 24 hours using 0.5 ml serum-free medium with high glucose. After the cultured supernatant protein was quantified, mercaptoethanol-free protein sample loading buffer was added, cryopreserved at −80° C. Water was used to prepare gelatin (Sigma-Aldrich, St. Louis, Mo.) into a concentration of 10 mg/ml, which was added to separation gel of protein electrophoresis according to the proportion of 1:10, causing the final concentration of gelatin as 1 mg/ml. Electrophoresis was performed in a voltage of 80V at 4° C. The gel was put into 0.25% Trixon-100 solution, and washing was performed twice in 30 minutes. And then the gelatin was added to incubation solution (50 mM Tris, 0.2M NaCl, 5 mM $CaCl_2$, 0.02% sodium azide), incubated for 24-48 hours at 37° C. Incubated gel was put into Coomassie brilliant blue to stain for 1-2 hours at room temperature, washed for 30 minutes with a solution having 30% methanol and 10% glacial acetic acid, a solution having 20% methanol and 10% glacial acetic acid, and a solution having 10% methanol and 5% glacial acetic acid, respectively, and then analyzed with Odyssey infrared fluorescence scanning system (LI-COR Biosciences, Lincoln, Nebr.). Both NMP-2 and NMP-9 are gelatinases, and can degrade gelatin; the places where gelatin is degraded are white, and other places are still black. Under normal conditions, both NMP-2 and NMP-9 exist in the form of zymogen, but after they are activated, zymogen is cleaved into activated protease. Therefore, both NMP-2 and NMP-9 are two white strips, the upper is zymogen form, and the lower is activated metalloproteinase. Activated or zymogen form of NMP-2 or NMP-9 can degrade gelatin, the results were shown in FIG. 4B, and naringenin or doxycycline gavage can reverse the increase of MMP-2 and NMP-9 caused by CaPO$_4$ daubing.

EXAMPLE 2

Naringenin Reduces the Onset of Abdominal Aortic Aneurysms in Mice Induced by Angiotensin II Firstly, 16 weeks of male ApoE$^{-/-}$ mice were randomly divided into two groups, control group (n=16) and naringenin group (n=15), respectively. And then they were anesthetized by 0.1% pentobarbital sodium, and mini pumps (model 2004, Alzet, Cupertino, Calif.) were subcutaneously submerged; angiotensin II (Sigma-Aldrich, St. Louis, Mo.) dissolved with normal saline was added to the pump, such that drugs can be continuously administered for 4 weeks at a dosage of 1000 ng/kg/min. From the first day after surgery, gavage was daily performed to mice at constant time points, water gavage in control group, and naringenin gavage (50 mg/kg) in naringenin group. Materials were removed 28 days after gavage. Blood pressure of the mice was measured by tail cuff method with BP-89A sphygmomanometer (Beijing Softron Biotechnology Co., Ltd.), and the mice were weighted. Blood was drawn in inner canthus of the mice, and after centrifuged for 10 minutes at 6000 rotations, supernatant was removed and the blood fat levels of the mice were measured. Naringenin reduces the levels of cholesterol, triglyceride, and low density lipoprotein in mice, which corresponds to the previous report, but it does not have an effect on the blood pressure and body weight of the mice, see Table 2.

TABLE 2 biochemical indexes of angiotensin II submerging pump induced ApoE$^{-/-}$ knockout mice

| Group | AngII | AngII + NGN |
|---|---|---|
| Number | 14 | 14 |
| Body weight (g) | 28.8 ± 1.42 | 28.9 ± 2.03 |
| Cholesterol (mmol) | 12.3 ± 1.36 | 8.46 ± 2.45 * |
| Triglyceride (mmol) | 1.66 ± 0.62 | 0.69 ± 0.35 * |
| Low density lipoprotein(mg/deciliter) | 88.9 ± 45.7 | 44.1 ± 15.9 * |
| High density lipoprotein (mg/deciliter) | 55.3 ± 5.35 | 56.5 ± 5.97 |
| Blood pressure (mmHg) | 131.0 ± 16.20 | 136.6 ± 14.27 |

Figure 5:
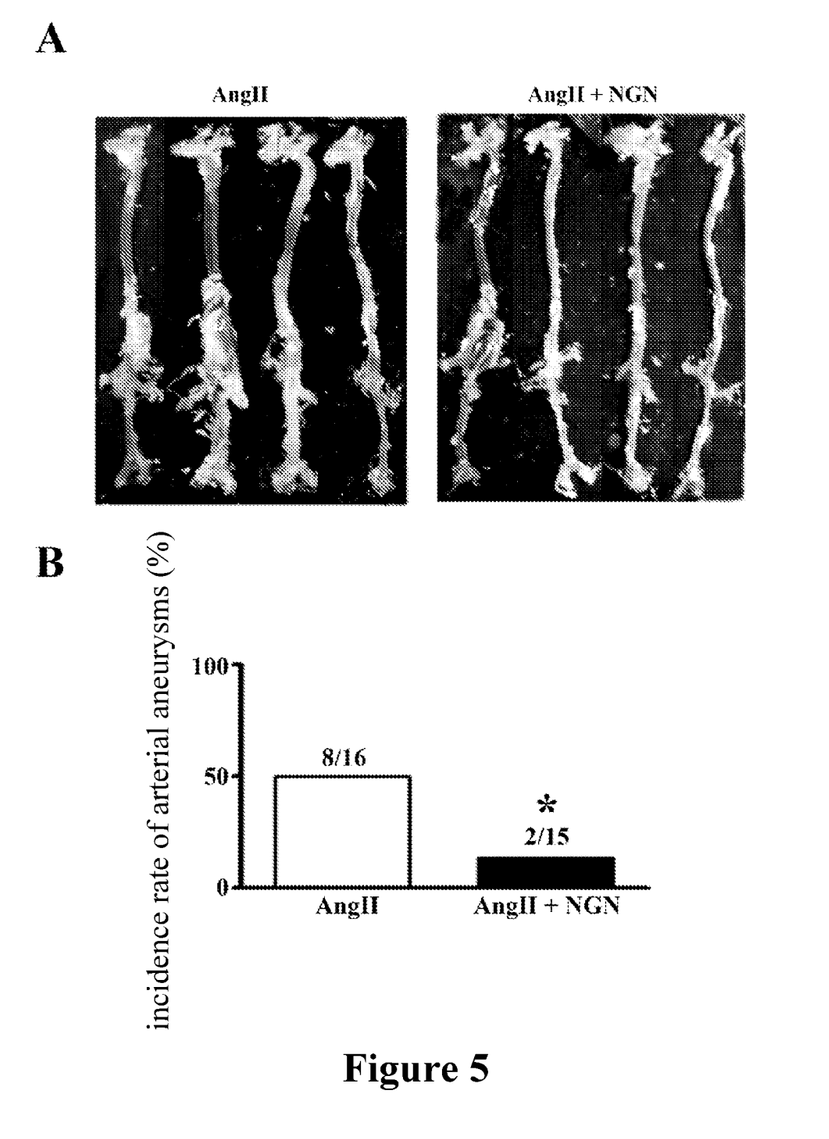
FIG. 5 shows the reduction of the onset of abdominal aortic aneurysms in angiotensin II induced $ApoE^{-/-}$ mice by naringenin gavage.

Aortas of mice were fixed and separated. AngII group was the control group of angiotensin II submerging pump and water gavage. AngII+NGN group was the group of angiotensin II submerging pump and naringenin gavage. Four blood vessels were randomly selected in each group for photographing. The results were shown in FIG. 5A, the former two blood vessels in AngII group have significant bulges at suprarenal site, exceeding 50% of the diameters of the blood vessels at adjacent site, and arterial aneurysms are formed. However, in naringenin gavage group, there are arterial aneurysms formed at suprarenal site only in the first blood vessel, while there are no arterial aneurysms formed in the remaining three blood vessels, showing that naringenin gavage can reduce the formation of abdominal aortic aneurysms of mice induced by angiotensin II.

Next, the statistics of the onset of abdominal aortic aneurysms in all the mice was performed. In the control group of angiotensin II submerging pump and water gavage, only one of 16 mice died from the fracture of aortic dissection within the first 7 days after submerging pump, another one died from the fracture of abdominal aortic aneurysms 1 week after submerging pump, abdominal aortic aneurysms were generated in 6 of the remaining 14 mice at 28th day after submerging pump. Therefore, in control group of angiotensin II submerging pump, aortic aneurysms were formed in 8 of 16 mice, that is, the morbidity of aortic aneurysms was 50%. And in the group of angiotensin II submerging pump and naringenin gavage, 1 of 15 mice died from the fracture of aortic aneurysms, only 1 of the remaining mice suffered from abdominal aortic aneurysms at 28 day after submerging pump. Therefore, in the group of angiotensin II submerging pump and naringenin gavage, only two of 15 mice suffered from aortic aneurysms, that is, the morbidity of aortic aneurysms was 13.3%. These show that naringenin gavage can significantly reduce the onset of angiotensin II mediated aortic aneurysms of mice, see Table 3. Statistical situation of the onset of aortic aneurysms was shown in FIG. 5B.

TABLE 3

Onset situation of aortic aneurysms in ApoE$^{-/-}$ mice with water/naringenin gavage mediated by angiotensin II

| Group | Number | Dissection | Fracture | aneurysm | Without aneurysm |
|---|---|---|---|---|---|
| AngII | 16 | 1 | 1 | 6 | 8 |
| AngII + NGN | 15 | 0 | 1 | 1 | 13 |

EXAMPLE 3

Naringenin can Reduce the Severity of Aortic Aneurysms

Figure 6:
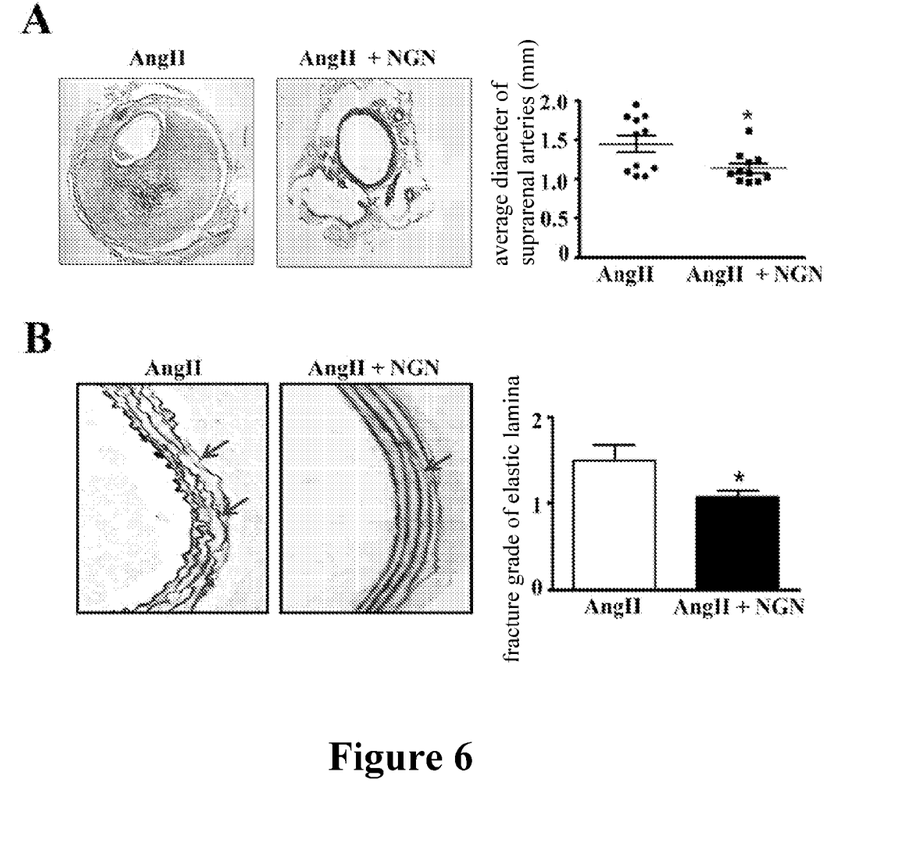
FIG. 6 shows the reduction of the severity of abdominal aortic aneurysms in angiotensin II induced $ApoE^{-/-}$ mice.

After removing materials from mice, aortas were perfused with 4% paraformaldehyde and fixed, the suprarenal aorta from diaphragm muscle to renal artery branch on the right side was equally divided into two segments, which were put into liquid nitrogen to freeze for 30 s after embedded with OCT. Serial sections were performed, the thickness of each section was 6 μm, with the spacing of 300 μm, and continuous 16 sections were performed on each mouse. H.E. staining was used to determine the diameters of abdominal aortas of mice, the diameters were measured and the maximum diameter was selected therefrom. The maximum diameter was compared with the diameter of adjacent site, and if the maximum diameter exceeds 50% of diameter of the adjacent site, it can be considered that the mouse suffered from an abdominal aortic aneurysm. FIG. 6A shows the maximum diameter of suprarenal abdominal aortas of survived mice with naringenin or water gavage after angiotensin II submerging pump, and each group has 11 mice. The result shows that the maximum diameter of abdominal aortas of mice significantly decreases after naringenin gavage.

We used Gomori staining to determine the fracture situation of the elastic lamina of abdominal aortas of mice, and statistics was performed. The results were shown in FIG. 6B, the fracture of the elastic lamina of abdominal aortas of mice decreases after naringenin gavage, and the mice detected in each group are all 6 mice. The data in Figure are an average value ±standard deviation.

These results show that naringenin gavage can significantly reduce the onset and severity of abdominal aortic aneurysm of mice mediated by angiotensin II.

EXAMPLE 4

Figure 7:
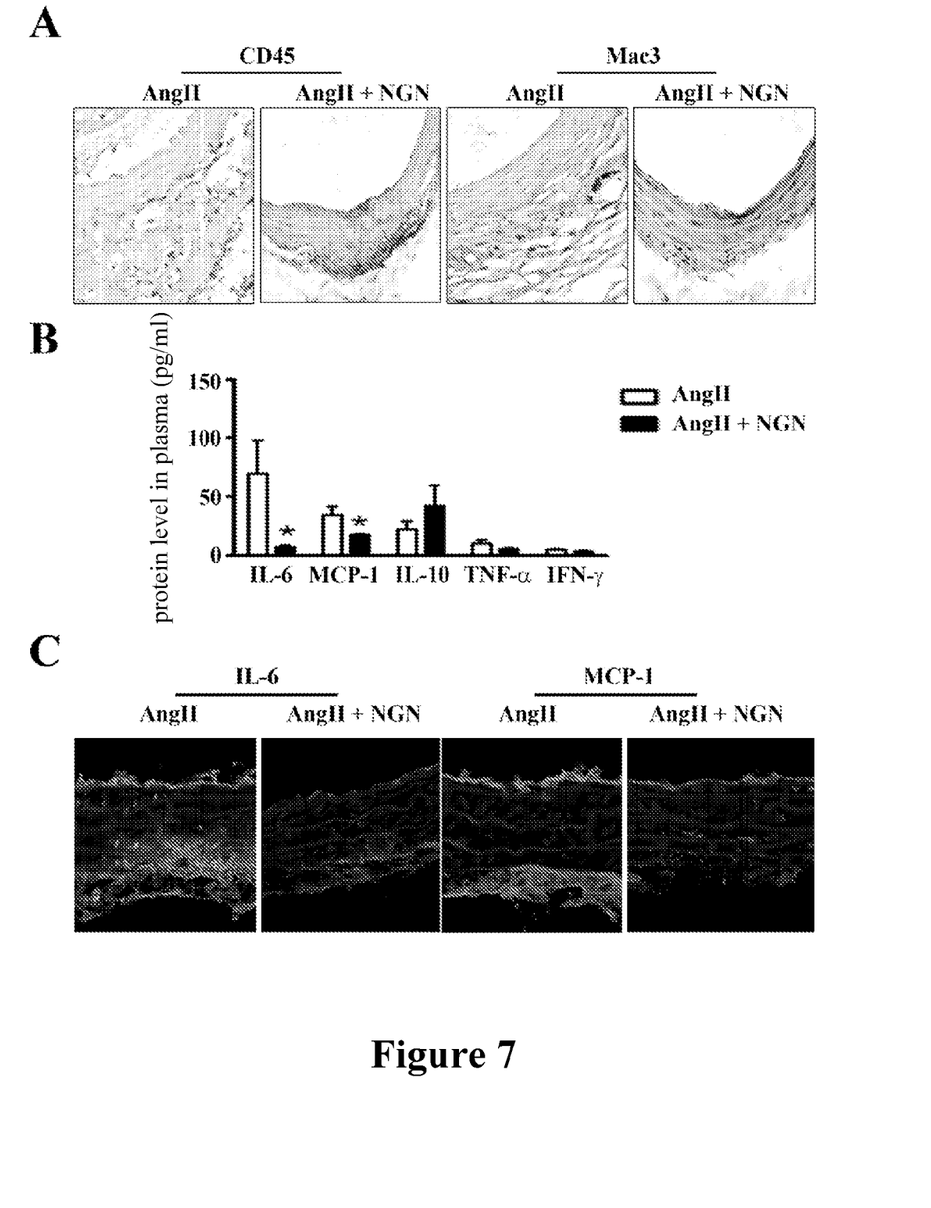
FIG. 7 shows the reduction of the inflammation degree of vascular walls of suprarenal aortas in angiotensin II induced $ApoE^{-/-}$ mice by naringenin gavage.

Naringenin Gavage can Reduce Inflammatory Response of Blood Vessel in Mice Mediated by Angiotensin II 1. Naringenin Inhibits Inflammatory Cell Infiltration of Vascular Wall CD45 and Mac3 were results of immunofluorescent staining on anti-Mac3 specific antibody and anti-CD45 specific antibody, respectively. The results were shown in FIG. 7A, compared with the control group of water gavage, naringenin gavage can significantly reduce the infiltration of inflammatory cell (macrophage and leukocyte) in adventitia.

2. Naringenin Reduces the Levels of IL-6 and MCP-1 in Plasma

Eyeballs of mice were removed and blood was drawn, 20 μl of heparin was added into the blood, after centrifuged at 6000 rotations and 4□ for 10 minutes, the supernatant was aspirated. 10 μl of supernatant was taken, and 10 μl of beads were added, and then 10 μl of PE was added, washed twice with lotion after incubating for 2 hours at room temperature, and then 200 μl of lotion is added. Sorting was performed in the manner of up-flowing after blending (wherein, the flow kits of inflammatory factors of mice were purchased from BD Company). The results were shown in FIG. 7B, and after naringenin gavage, the levels of IL-6 and MCP-1 in plasma significantly decrease (n=11, P<0.05). Meanwhile, anti-inflammatory factor, IL-10, does not change significantly, while TNF-α and IFN-γ do not change, either.

3. Naringenin reduces the expressions of IL-6 and MCP-1 in vascular walls

In order to illustrate the mechanism by which naringenin reduces inflammatory reaction of abdominal aorta vascular walls of mice, immunofluorescent staining was performed on IL-6 and MCP-1 by continuous sections to analyze their distributions and expressions in vascular walls. Confocal fluorescence microscope was used to irradiate, green light showed IL-6 or MCP-1, and blue light showed cell nucleus. The results were shown in FIG. 7C, and when naringenin gavage is performed on mice, the production of IL-6 and MCP-1 in vascular walls significantly decreases, illustrating that naringenin can reduce the contents of IL-6 and MCP-1 in vascular walls.

4. Naringenin Gavage Reduces the Activity and Expression of Metalloproteinase in Mice The results were shown in FIG. 8A, and after using angiotensin II to perfuse, the activity of metalloproteinase in mesolamella and adventitia is high, while after naringenin gavage, activated metalloproteinase significantly decreases.

Figure 8:
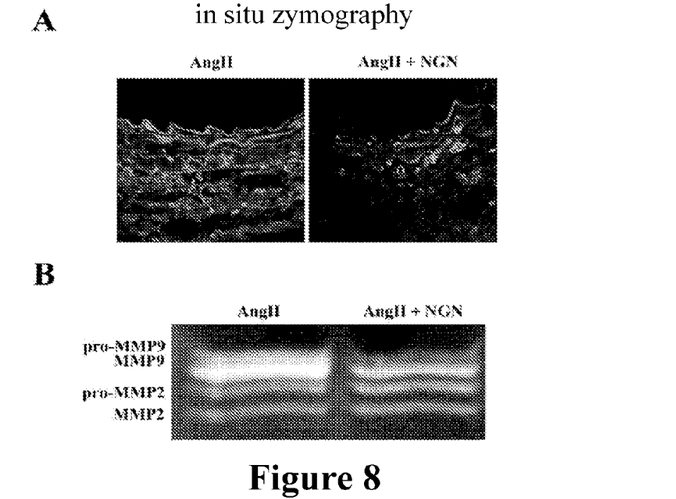
FIG. 8 shows the reduction of the activities of matrix metalloproteinases in vascular walls of suprarenal arteries in angiotensin II induced $ApoE^{-/-}$ mice by naringenin gavage.

The results were shown in FIG. 8B, and after using naringenin gavage, zymogen form of MMP-9 significantly decreases, that is, naringenin inhibits the synthesis of MNP-9, but meanwhile, the active form of NMP-9 and NMP-2 do not change significantly.

EXAMPLE 5

The Effect of Naringenin on Development and Outcome of Formed Abdominal Aortic Aneurysms $CaPO_4$ daubed mice model and angiotensin II induced mice model were respectively used to explore whether naringenin on formed aortic aneurysm functions or not.

Figure 9:
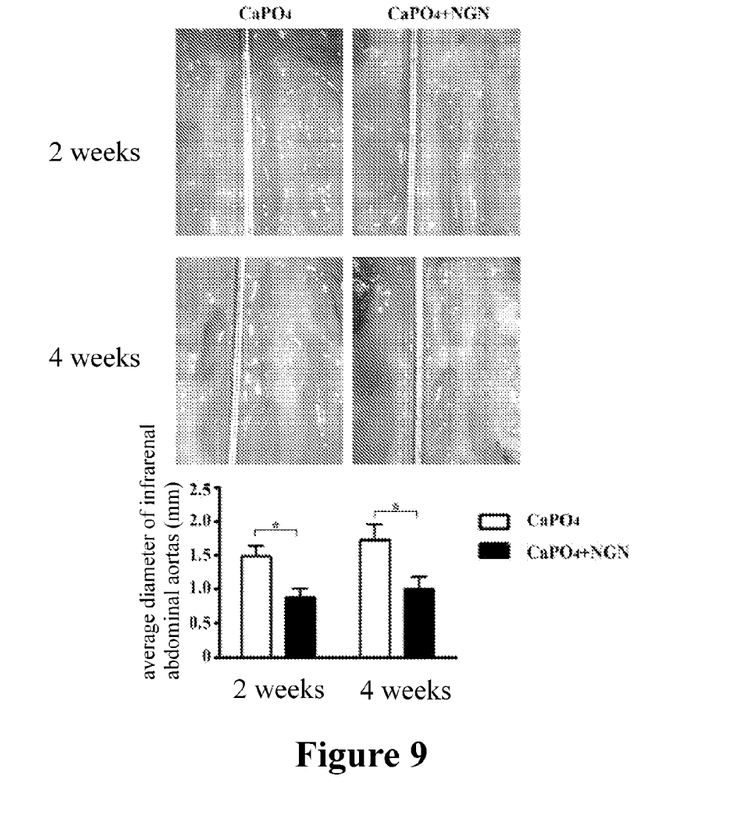
FIG. 9 is a series of figures of abdominal aortas and statistical graph of diameters thereof measured ex vivo of 12 weeks of male C57 mice in Example 5, wherein the mice were daubed with $CaPO_4$ for 7 days, and then were gavaged with naringenin (50 mg/kg/day) and water for 2 weeks and 4 weeks, respectively.
Figure 10:
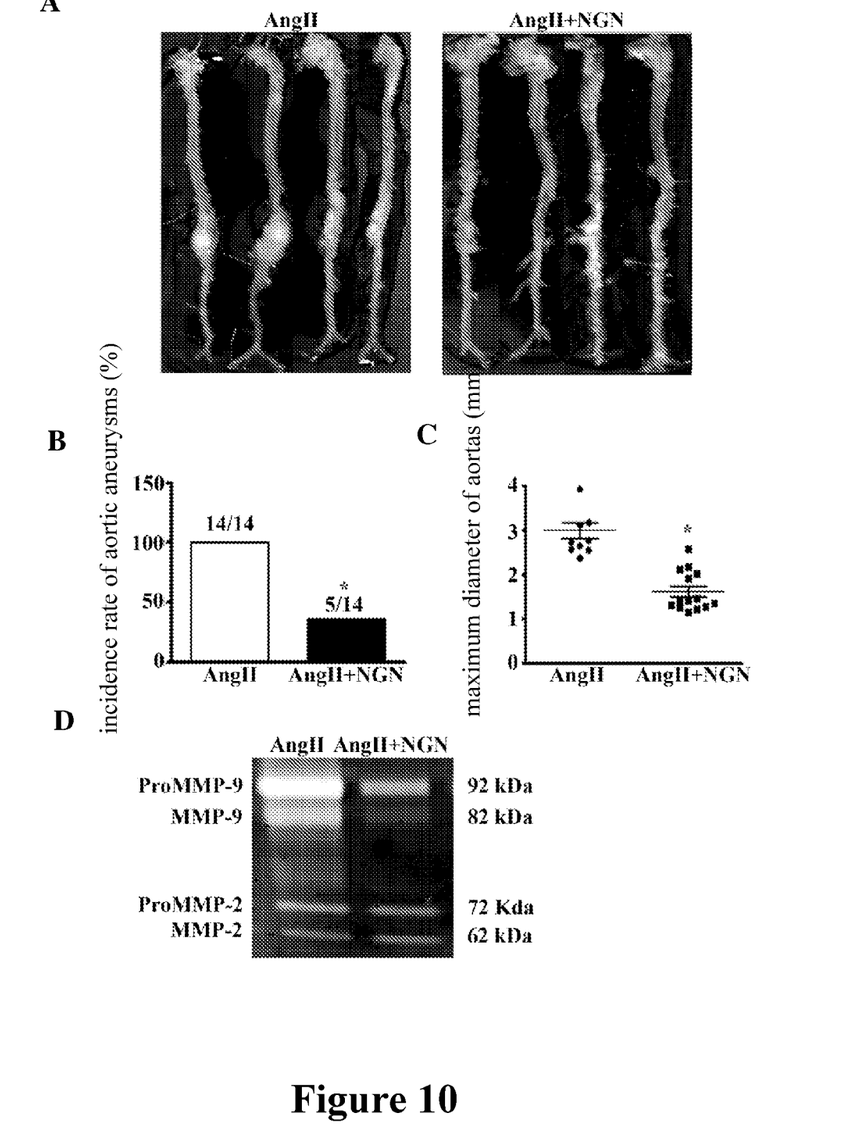
FIG. 10 is a series of figures of 20 weeks of male ApoE knockout mice in Examples, wherein the mice were given angiotensin II submerging pump treatment for 28 days and a ultrasonic testing was performed, and the mice in which aneurysms had formed were equally divided into two groups to feed on naringenin or water, and were given another angiotensin II submerging pump treatment for 28.

In $CaPO_4$ model, we daubed $CaPO_4$ at infrarenal abdominal aortas in 12-week old of male C57 mice (totally 36 mice), and arterial aneurysms were formed 7 days later. Next, the 36 mice were randomly divided into 2 groups: one group was given naringenin (50 mg/kg/day) gavage, and another group was given equal water gavage. Gavage was performed for 2 weeks (8 mice for each group) and 4 weeks (10 mice for each group), respectively. We found by ex vivo measuring method (the results were shown in FIG. 9), that, compared with control group, naringenin can significantly inhibit the progression of arterial aneurysms and reduce the average diameter of infrarenal abdominal aortas (2 weeks, 0.884±0.33 vs. 1.488±0.42 mm, P<0.05; and 4 weeks, 0.9935±0.5 vs.1.718±0.64 mm, P<0.05).

In addition, we used the method of angiotensin II subcutaneous submerging pump for 28 days (1,000 ng/kg/min), to induce abdominal aortic aneurysms on 20 weeks of male ApoE knockout mice (totally 40 mice) and used ultrasound to detect the diameters of the abdominal aortas. The diameter greater than 50% of diameter of adjacent blood vessel was used as a standard of the onset of an aortic aneurysm, and 28 mice suffered from aortic aneurysms 28 days later.

Similar maximum abdominal aorta diameter was used as grouping standard, and we equally divided the mice which suffered from aortic aneurysms (28 mice) and did not suffer from aortic aneurysm (12 mice) into two groups, the average maximum abdominal aorta diameters were equal; one group was given naringenin gavage, and the other group was given equal water gavage.

Angiotensin II submerging pump was continuously given to all the mice for 28 days. The same results as in the $CaPO_4$ model were observed: in the mice which did not suffer from aortic aneurysms previously, only one mouse in 6 mice by naringenin gavage suffered from aortic aneurysms 28 days later (with the incidence rate of 16%), while 3 mice in control group suffered from aortic aneurysms (with the incidence rate of 50%). In the mice which had suffered from aortic aneurysms previously, 4 mice in the 14 mice by water gavage died from fracture of aortic aneurysms, the other 10 survived mice all suffered from serious aortic aneurysms (the average diameter reaches 3.00±0.58 mm). In contrast, after the second round of angiotensin II simulation, the mice in naringenin gavage group all normally survived. In these 14 mice, aortic aneurysms were observed in only 5 mice, and the aortic aneurysms in the remaining mice were all reversed, and the maximum diameter of the blood vessels was reduced to 1.62±0.45 mm. In addition, we found by using gelatin zymography to detect the activity of metalloproteinase that naringenin can significantly inhibit the activity of metalloproteinase NMP-9.

In sum, naringenin not only can inhibit the formation of abdominal aortic aneurysms, but also can reverse the formed aortic aneurysms so as to exert a therapeutic effect.

INDUSTRIAL APPLICATION

The drugs for preventing and/or treating abdominal aortic aneurysms provided by the present invention are safe and low toxic, and the pharmacologic effects thereof are stronger; sources of raw materials thereof are rich, wide, inexpensive, and can be obtained from crude product or monomer of Naringin by a hydrolysis method, or obtained by extracting from various crude medicines containing naringenin, or obtained by using other chemical synthesis methods; the cost is low, the process is simple, and the yield is high; and the curative effect is definite, and the effective dose is low. The present invention provides a new drug source for preventing, diagnosing, detecting, protecting, treating, and studying abdominal aortic aneurysm diseases, it is easy to popularize and apply, and it can produce huge social and economic benefits within a short period of time.

What is claimed is:

1. A method of reducing onset of or treating abdominal aortic aneurysms in a subject, the method comprising:
   administering an effective amount of a composition comprising naringenin to the subject, wherein the subject is in need of such reduction or treatment.

2. The method of claim 1, wherein the composition is in a form of a drug or a health care product.

3. The method of claim 1, wherein the method achieves one or more effect selected from the group consisting of:
   inhibiting fracture of abdominal aorta elastic lamina in the subject;
   inhibiting infiltration of inflammatory cells of abdominal aorta vascular walls in the subject;
   inhibiting levels of interleukin IL-6 and monocyte chemotactic factor MCP-1 in plasma in the subject;
   inhibiting expression of inflammatory factors in abdominal aorta vascular walls in the subject; and
   inhibiting activity and expression of a matrix metalloproteinase of abdominal aorta vascular walls in the subject.

4. The method of claim 3, wherein the method achieves the effect of inhibitin expression of inflammatory factors in abdominal aorta vascular walls in the subject, and wherein the inflammatory factors comprise interleukin IL-6 and monocyte chemotactic factor MCP-1.

5. The method of claim 3, wherein the method achieves the effect of inhibiting infiltration of inflammatory cells of abdoniminal aorta vascular walls in the subject, and wherein the inflammatory cells comprise macrophage and/or leukocyte.

6. The method of claim 3, wherein the method achieves the effect of inhibiting-activity and expression of a matrix metalloproteinase of abdominal aorta vascular walls in the subject, and wherein the matrix metalloproteinase comprises NMP-9.

* * * * *